United States Patent [19]

Schmittmann

[11] 4,350,688

[45] Sep. 21, 1982

[54] PROCEDURE FOR MANUFACTURING SAPONINE EXTRACT

[75] Inventor: Hans B. Schmittmann, Velbert, Fed. Rep. of Germany

[73] Assignee: Dr. H. Schmittmann GmbH, Velbert, Fed. Rep. of Germany

[21] Appl. No.: 104,792

[22] Filed: Dec. 18, 1979

[30] Foreign Application Priority Data

Jan. 5, 1979 [DE] Fed. Rep. of Germany ....... 2900304

[51] Int. Cl.³ .................... A61K 31/705; C07J 17/00
[52] U.S. Cl. ............................. 424/182; 260/236.5; 536/5
[58] Field of Search ........................... 424/182; 536/5; 260/236.5

[56] References Cited

U.S. PATENT DOCUMENTS

| | | | |
|---|---|---|---|
| 2,411,631 | 11/1946 | Miescher et al. | 536/5 |
| 3,170,916 | 2/1965 | Dziengel | 536/5 |
| 3,883,425 | 5/1975 | Dorn | 536/5 |
| 3,886,272 | 5/1975 | Parkhurst et al. | 536/5 |
| 3,901,875 | 8/1975 | Park | 536/5 |
| 3,933,789 | 1/1976 | Pegel | 536/5 |
| 4,084,010 | 4/1978 | Takemoto et al. | 536/5 |
| 4,157,894 | 6/1979 | Bombardelli | 536/5 |

*Primary Examiner*—Johnnie R. Brown
*Attorney, Agent, or Firm*—Friedman, Goodman & Teitelbaum

[57] ABSTRACT

A saponine extract product which is a granulate in pellet form, the granules being pourable and having low hygroscopicity. A process for producing a pourable granular saponine extract product of low hygroscopicity comprising granulizing a saponine extract in a fluidized bed.

8 Claims, 5 Drawing Figures

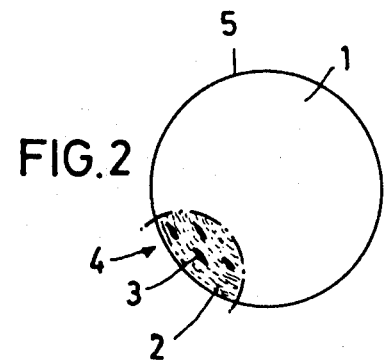
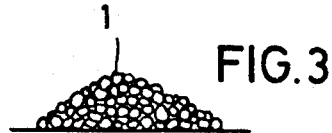
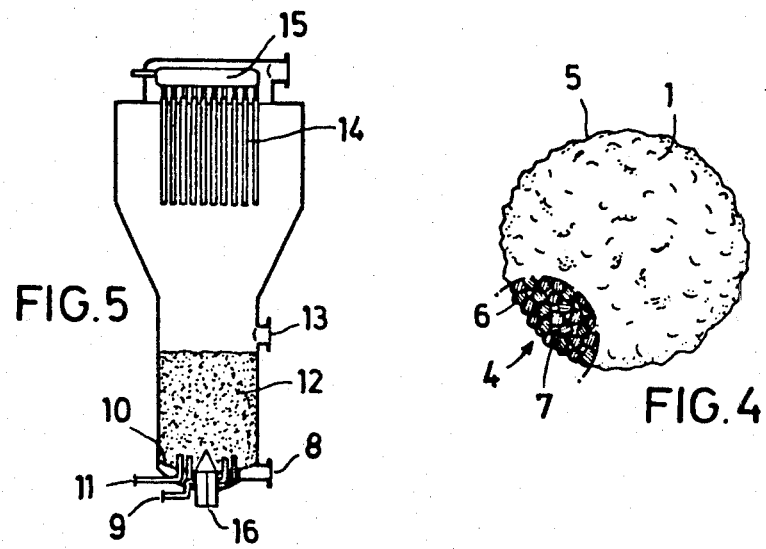

PROCEDURE FOR MANUFACTURING SAPONINE EXTRACT

The invention concerns a saponine extract product as well as a procedure for its manufacture.

Saponines are foam building glucoside substances. As the content material of numerous plants, the saponines are spread widely throughout the world. Their obtention results from extraction and preparation processes determined by the drug. In general, the termination of the processing apparatus is the transfer of the extracts into a powder form. In this form, the saponines are available in commerce.

In those cases where it is not possible to transform the saponine extracts into a powder form, they are offered in strong concentrated, liquid form.

The saponines obtained from different saponine containing drugs are more or less different. A chemical distinction is made on the basis of their sugar-free basic structure, the so-called aglycone or also sapogenin. In this the two large groups that have to be distinguished are:

1. Sapogenin with triterpine structure (oleanolic acid-basic structure)
2. Spirostanole (steran structure-digitogenine).

Saponines are highly desired as healing and washing agents. At the present, the use of saponines has shifted more to other application areas.

For example, saponine is obtained from quillayae saponaria. It is a drug extract that has been cleaned in a special manner and made into a powdered form of high value and soluble in any proportion in water. The principal saponine designated in the saponine part, quillaya saponine, is a glucoside whose aglycone as a triterpinoid belongs to the $\beta$-amyrine-oleanic acid group. The sugars released in an hydrolysis are at the present not known individually. Quillaya saponine works hemolytically. When breathing in, the powder irritates the mucuous skin. It is used principally for the manufacture of film emulsions and is free from heavy metals and hardening components. As powder it is white to very white and on top of being soluble in water it is soluble in dioxane. The 5% watery solution is quite water clear and has a pH-value between 4 and 5. The stability of the saponine solution in an open container and at an outside temperature of 15° C. averages 3–5 days. The stability is prolonged with temperatures below 10° C. and is shortened at temperatures above 20° C. The stability of the solution can also be prolonged through storage in cooling rooms, boiling and storage in a closed container, the addition of ethyl alcohol up to 18% or the addition of a conservation agent.

The incorporation of conservation agents, however, substantially changes the natural composition of the solution.

Gypsophila saponine is generally obtained from the radix saponaria and also as a drug extract in powder form. It is—like the quillaya saponine—useable for the manufacture of film and photographic paper and in this shows the same characteristics. Furthermore, it is used primarily as a wetting agent in the cosmetic and the galvanic industry and is used in the pharmaceutical industry to advance the intake of medications.

Further areas of application of the saponine and depending on the degree of purity are the food industry, the lacquer and paint industry, the reproduction industry, the beverage industry and the use for cleaning purposes.

In most cases saponine is used to influence the surface tension of fluids and the like.

The essential disadvantage of the extracts that are available on the market is their difficult manipulation. In powder form, it severely irritates the mucuous linings. A solution is stable for a long period of time only after special measures are taken. A special disadvantage is presented by the strong hygroscopicity of the saponine powder. It has a tendency to clotting under the influence of humidity. A clotted saponine can be processed only with some difficulties and is the subject frequently therefore of complaints.

The task of the invention is the creation of a dust-free saponine extract product, which shows the saponine concentration present in the known powder, which is easy to manipulate and which without special preparatory measures and without modifications can be stored in the air.

This task is solved through a saponine extract product that consists of a granulate in pellet form. The bulk density of the granulate amounts in particular to 0.5 to 0.9 $g/cm^3$. With regards to a bulk density of the powder of 0.3 $g/cm^3$, this substantially higher bulk density of the granulate signifies a substantial technical advance, as per volume unit a substantially higher quantity can be handled. Preferred is a granulate with granules with a diameter in the 0.3 to 2 mm range and a granular shape that is essentially round, respectively conical shaped. This formation of the granulate kernels as well as the surprising characteristics that the granulate at a similar humidity, when compared with the dry commercially available powder, is practically no longer hygroscopic permit a satisfactory sprinkling ability which cannot be guaranteed with a powder.

The granulate distinguishes itself from the commercially common saponine extract products in that its hydroscopicity is substantially reduced and that even under the influence of air humidity it remains capable of sprinkling for a long period of time.

Preferably the pellet kernel shows a smooth, sinter-like, specifically glazing like surface. Its construction material is X-ray amorph and its structure is radially layered, i.e. in a layer like manner it is built of several spherical shells. Another also inventive construction consists in the fact that a large number of smaller primary kernels are connected to each other with their surfaces so that the granulate kernel represents a secondary form. The surface of such a granulate kernel is not as smooth as the kernel made out of spherical shells. It shows much more the contour of the primary kernels.

On top of the advantages that the higher bulk density with regards to the powders, special notice has to be given to the higher solubility of the saponine. On the basis of the strong inclination of saponine powder to bind with water there are formed clumps which in the manufacture of a solution, when necessary, have to be broken down by mechanical means. In contrast, the saponine granulate dissolves itself without clotting formation which was not to be expected. Up to now, it has not been possible to clarify on what rests the reduction of the strong hygroscopic characteristics in the granulate. It is surprising that the granulate is so little hygroscopic that it can be stored for a long time in open air without losing its sprinkling ability.

The manufacture of the inventive saponine granulate is derived from the common extraction procedures in which the drug is, in the usual manner, reduced and extracted and through precipitations, cleanings, and when necessary, sterilizations, shrinking and drying and thus prepared. In a known procedure, the drying can result through a spray drying. Furthermore, one has attempted to dry a foam and to mill the dry product or to make the powder into tablets or press-plate fragments. In all cases, however, one did not obtain a granulate in pellet form but a powder. Even the sometimes occuring intermediate product does not present a granulate form in the sense of the invention but in all cases an agglomerate which, however, like the powder, has a low bulk density and is hygroscopic to a high degree.

The inventively preferred procedure distinguishes itself in that the granulate formation is carried out in a fluidize bed. Although the technology has been known for a long time, granulate formation in a whirlpool, specifically a fluidized bed, was by no means evident. The high hygroscopicity of the dried saponine extract products lead to the assumption that the whirlpool bed would led to clumping and that no dry, free-flowing product could be obtained. In a surprising manner it was shown, however, that granulates with a continuous, constant bulk density were formed and that these granulated, essentially round particles were relatively hard but easily soluble in water. The granula size distribution can be controlled so that final products can be manufactured that have a desired granular size and in which the granular size can be very small. In an intimate and mixing of dry and fluid components coupled with intensive drying and the associated cooling, a controlled granule formation is obtained. Evidently this is possible since the granulate kernels unexpectedly lose their strong hygroscopicity, a phenomenon which at the time could not yet be explained.

For the manufacture of the inventive saponine granules not every known fluidize bed procedure is appropriate. Much more, the described conditions have to be fulfilled in order to ensure the granulation. So far a discontinuously working reactor has been shown to be advantageous because it makes possible the injection of the vaporized, fluid saponine extract in the bottom of the reactor in the fluidize bed sew that the rays permit an additional mixing effect and an intensive contact between the vaporized fluid and the solid. Suitably, a saponine solution which preferably contains 20 to 50 weight-% saponine, is injected.

Further essential procedure steps are described in connection with FIG. 5 hereafter.

On the basis of the drawing, the invention is further clarified. They are:

FIG. 1 a saponine granulate heap,

FIG. 2 schematically the structure of a kernel of the heap in FIG. 1;

FIG. 3 another saponine granulate heap;

FIG. 4 schematically the structure of a kernel from the heap in FIG. 3;

FIG. 5 a reactor for the manufacture of the saponine extract.

The heap in FIG. 1 clarifies that the saponine kernels 1 are within a narrow kernel size range. They show preferably a diameter of 0.3-2 mm. FIG. 2 clarifies the spherical scale structure of a granulate kernel. The kernel 1 is essentially spherical and has spherical scales 2 which, in a layer-like manner, are located upon each other. Between the layers there can be provided pores 3 which, however, corresponding to the layer limits are formed in an elongated manner. Thus, in the cut image 4 of the kernel 1, there is shown a very characteristic layer texture to which also the pore shapes have been adapted.

In contrast the saponine kernels in the heap in FIG. 3 are somewhat less round than the kernels in the heap in FIG. 1. The kernel size, however, does correspond to that of the kernels in FIG. 1. FIG. 4 clarifies the structure of the granulate kernels. The surface 5, which in the granulate kernel in FIG. 2 is smooth, shiny and sealed, is in the granulate kernel of FIG. 4 and shows the contours of the primary kernel 6. It is made up of numerous irregularly formed primary kernels 6 whose surfaces are connected with each other so that pores 7 are formed, as shown in the cut-out section of FIG. 4. Both granular shapes have very good pourability and retain this quality even after prolonged storage in open air. This means that the hygroscopicity has been reduced in such a manner that the adhering or the clumping of the kernels in the heap does not take place. Thus, the product can no longer be described as hygroscopic.

In a preferred procedure for the manufacture of the inventive saponine granulate, a reactor according to FIG. 5 is used. It corresponds to a common construction type. At 8 the low pressure—fluidization air for the fluidized bed is brought under a perforated bottom through which the air flows into the reaction space by means of which the material is fluidized. The fluid saponine extract enters through 9 in the vaporizer 10 and is atomized. For this purpose, high-pressure vaporizing air which enters into the vaporizing space through the pipes 11 that are located underneath the fluidization space 12 is used. The vaporizer 10 is installed in such a manner that the vaporized fluid flows directly from below in the fluidized bed. Saponine powder and/or other common solid powders are brought into the fluidize bed 12 at 13. Solid material dust can be collected in the filter 14 and the air is removed at 15. After the completion of the granulation, i.e. after the obtention of the desired granular kernel size, the saponine granulate is let out at 15.

It was shown that the variation of the common fluidize bed procedure parameters does not affect the granulation of the saponines in the common manner. So far the use of the procedure had, until now, no results. It could surprisingly be determined that high fluidized bed temperatures form very fine parts which in general do not shown the desired optimal characteristics and lead to clumping. Only the lowering of the commonly used fluidized bed temperature brings about the desired result. Clearly, until now the expert for the obtention of a high efficiency and the economics of the reactor was inclined to select high temperatures for the fluidized bed. To this has to be added that until now in the known application of the fluidized bed procedure generally other procedure parameters for the size of the granulate kernel were used. That in the present case the fluidized bed temperature exerted this specific influence was not to be expected and until now unknown. Thus the inventively preferred procedure distinguishes itself in particular by the fact that the granulation takes place at fluidize bed temperatures of 40°-80° C., in particular 45°-60° C. Preferably with this are injected 20 to 50% saponine extract solutions which in particular show temperatures of 3°-10° C. The heated air in the fluidize bed is preferably introduced with temperatures of 120°-170° C. The quantity of dried powder amounts to 0-80 weight-% taken on the vaporized solution quantity, preferably 10-30 weight-%.

Instead of the dried powder or together with dried powder it is possible that other additive material in identical quantities can be added above and/or underneath in the whirlpool bed. The quantity is determined by the desired purity degree of the saponine extract. Suitably in this connection, continuously or for the conclusion of the step-like executed procedure an hydrophobic agent can be added to the fluidize bed, preferably from above, so as to make the final product hydrophobic. The hydrophobic product can be stored without limitations and is satisfactorily pourable.

The procedure for the manufacture of the inventive product is described by means of specifically known procedure which works in a discontinuous manner and in which one would inject in the bottom of the fluidize bed. After, however, the surprising influence of the fluidize bed temperature is discovered, also other known fluidize bed procedures can be transformed in such a manner that the inventive product can be manufactured. To that extend, the procedure for the manufacture of the inventive product is not limited only to the discontinuous working procedure.

I claim:

1. A process for producing a pourable granular saponine extract product of low hygrosopicity comprising granulzing a saponine extract in a fluidized bed obtained by means of low pressure fluidization air, wherein a solution of said saponine extract is injected in said fluidized bed by means of high pressure vaporization air from directly below said fluidized bed and the temperature of said fluidized bed is from 40° C. to 80° C.

2. A process according to claim 1 wherein additional solid materials are injected into the fluidized bed from above.

3. A process according to claim 1 wherein the temperature of the fluidized bed is from 45° to 60° C.

4. A process according to claim 1 wherein a solution of said saponine extract having a concentration of 20-50% is injected in said fluidized bed from below.

5. A process according to claim 1 wherein the low pressure fluidization air is introduced at temperatures from 120° to 170° C.

6. A process according to claim 1 wherein a saponine extract powder of 0-80 weight percent, based on the vaporized solution quantity is added.

7. A process according to claim 6 wherein the saponine powder is 10-30 weight percent.

8. A process according to claim 2 wherein said additional solid materials are introduced in quantities of 0-80 weight percent based on the vaporized solution quantity.

* * * * *